United States Patent [19]

Daniel

[11] Patent Number: 4,523,592
[45] Date of Patent: Jun. 18, 1985

[54] ANASTOMOTIC COUPLING MEANS CAPABLE OF END-TO-END AND END-TO-SIDE ANASTOMOSIS

[75] Inventor: Rollin K. Daniel, Birmingham, Ala.

[73] Assignee: Rollin K. Daniel P.S.C., Louisville, Ky.

[21] Appl. No.: 488,182

[22] Filed: Apr. 25, 1983

[51] Int. Cl.³ .............................................. A61B 17/04
[52] U.S. Cl. .................................................. 128/334 C
[58] Field of Search ............... 128/334 C, 334 R, 305, 128/328, 346

[56] References Cited

U.S. PATENT DOCUMENTS

| | | | |
|---|---|---|---|
| 1,151,300 | 8/1915 | Soresi | 128/334 C |
| 3,155,095 | 11/1964 | Brown | 128/334 C |
| 3,166,072 | 1/1965 | Sullivan, Jr. | 128/346 |
| 3,254,650 | 6/1966 | Collito | 128/334 C |
| 3,254,651 | 6/1966 | Collito | 128/334 C |
| 3,316,914 | 5/1967 | Collito | 128/334 C |
| 4,294,255 | 10/1981 | Geroc | 128/334 C |
| 4,366,819 | 1/1983 | Kaster | 128/334 C |

FOREIGN PATENT DOCUMENTS 2657255 6/1978 Fed. Rep. of Germany ... 128/334 C

OTHER PUBLICATIONS

Bickham's "Operative Surgery", vol. 2, p. 12, 1924.
An Experimental Method for Nonsuture Anastomosis of the Aorta, Surgery, Gynecology, and Obstetrics, vol. 119, No. 2, pp. 362-364.

Primary Examiner—C. Fred Rosenbaum
Assistant Examiner—Gene B. Kartchner
Attorney, Agent, or Firm—Silverman, Cass & Singer

[57] ABSTRACT

Anastomotic coupling means capable of both end-to-end and end-to-side anastomosis without resorting to suturing. A pair of coupling disc members cooperate to couple the vessels, one of the members having spaced apart hook members and the other member having receptor cavities aligned with said hook members for locking the members together in a successful anastomatic procedure with tissue everted and secure on said hook members.

7 Claims, 15 Drawing Figures

ANASTOMOTIC COUPLING MEANS CAPABLE OF END-TO-END AND END-TO-SIDE ANASTOMOSIS

BACKGROUND OF THE INVENTION

This invention relates to surgical devices for anastomosis procedures requiring the union of luminal structures of the body, such as bile ducts and blood vessels, and more particularly, relates to coupling devices which eliminate the use of suture materials for coupling such vessels in surgical procedures.

In order to perform diversified anastomotic procedures without the use of sutures, coupling devices have been developed to secure the free ends of the tubular tissue members to be joined, as described in U.S. Pat. Nos. 2,453,056, 3,254,650, and 4,214,586. The anastomotic devices described in these patents are typically coupling tubes or rings adapted for attachment to the free ends of the tubular tissues which are everted to expose the luminal interior or intima of the ends of anastomotic repair.

U.S. Pat. No. 2,453,056 describes a three-piece anastomotic apparatus which can be employed to join the end of one vessel to the side of another vessel, but requires the portions of the incised sidewall of the second vessel to be held by multiple forceps while the end of the first vessel is inserted into the incision. Only thereafter can the incised portions of sidewall be mounted on the tubular member holding the everted end of the first vessel. The end-to-side anastomosis described in this patent is a portal caval shunt operation in which the end of a portal vein is joined to a vena cava. The complicated procedure requires multiple foreceps to hold the incised and everted wall of the vena cava, but in addition, the surgeon's finger must be placed under the vena cava during the insertion of the end of the portal vein which previously has been prepared by eversion upon a tubular device. Thus, the procedure requires not only holding the "cut lips" of the vena cava by the use of foreceps but, additionally, requires retention in the forceps in order to move the lips onto the tube carrying the end of the portal vein, and continued retention in the forceps during the subsequent securement of the lips on the tube by a clamping ring. Since only the end of the portal vein is secured on a coupling device prior to completion of the anastomosis junction, multiple instruments are required to manipulate the lips of the vena cava in order to complete the junction.

U.S. Pat. No. 3,254,650 does not teach side-to-end anastomosis but does describe a pair of "self-aligning" discs or sleeves 126 and 128 with preformed, alternating, axial pins 130 and axial passages 132 which receive the pins from the other disc (see FIGS. 10-22). The pins pierce the everted respective ends of the vessel to retain the ends thereon, and when the discs are pressed together, the everted ends are clamped between the discs. Subsequently, the protruding ends of the pins must be bent over in order to secure the discs together.

U.S. Pat. No. 4,214,586 also uses three elements for end-to-end anastomosis of tubular vessels. Here, to cylindrical adaptor are connected by a cylindrical sleeve-like member locking appendages which cooperate with gripper recesses for completing the anastomosis.

SUMMARY OF INVENTION

In accordance with this invention, coupling devices are especially constructed for enabling joinder of tubular tissues in either end-to-end anastomosis or in end-to-side anastomosis rapidly, efficiently and readily. Additionally, the coupling devices are provided with intergral, interlocking members which eliminate the necessity for a separate procedure in order to achieve this desired coupling or anastomosis of the vessels. The coupling devices comprise a pair cooperatively engageable plate or disc members having advantageously spaced and aligned hook means and receptor cavities for locking everted tissues of the vessels therebetween to achieve the desired anastomosis without resorting to suturing.

DESCRIPTION OF THE PREFERRED EMBODIMENTS

Referring to FIGS. 1 to 4, the annular coupler device is designated generally by the references character 10. A pair of the coupler devices 10 can be employed in either end-to-end anastomosis of tubular vessels or in end-to-side anastomosis without requiring any modifications in the couplers. Coupler device 10 also may be oval in configuration or of other suitable shape not interfering with the anastomosis.

Figure 1:
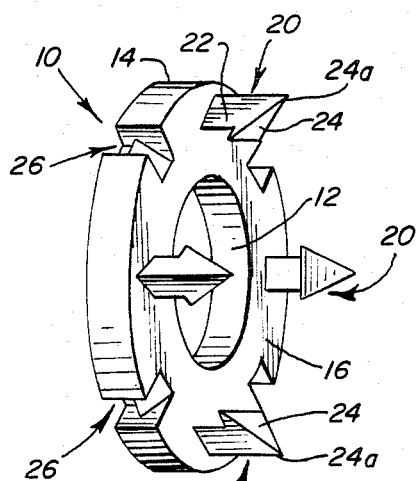
FIG. 1 is a perspective view of an anastomotic coupling device embodying the invention.
Figure 2:
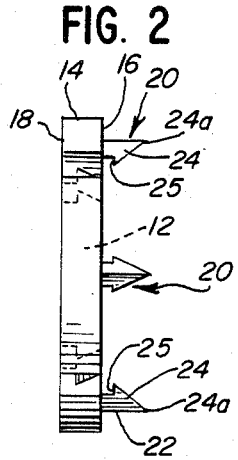
FIG. 2 is a side view of the device of FIG. 1, and illustrating the hook members projecting from one face of the coupler.

Referring particularly to FIG. 1, coupler device 10 is provided with an axial bore 12 therethrough. As best shown in FIG. 2, the width of the curved, peripheral surface 14 is less than the diameter of the annular coupler 10 in order to minimize the length of the bore 12 through which portions of the vessel must be guided in the anastomosis procedures as described hereinafter; particularly resulting vessel flaps in end-to-side procedure, as subsequently described. The coupler device 10 includes opposing front and rear, generally parallel, planar faces 16 and 18 respectively. Extending outwardly from front face 16 is a plurality of integrally formed, coupling hook members 20. In the illustrated embodiment, there are 4 hook members 20 equally spaced in a generally circular pattern upon the front face 16. Each hook member 20 includes a stud 22. At the remote end of the stud 22 is an integrally formed, wedge-shaped head 24. Head 24 includes a sharp tip 24a and an intermediate shoulder 25 formed radially inward from the stud 22. Tip 24a provides a barb-like tang for penetration of the vessel tissue in the anastomosis procedure.

Figure 15:
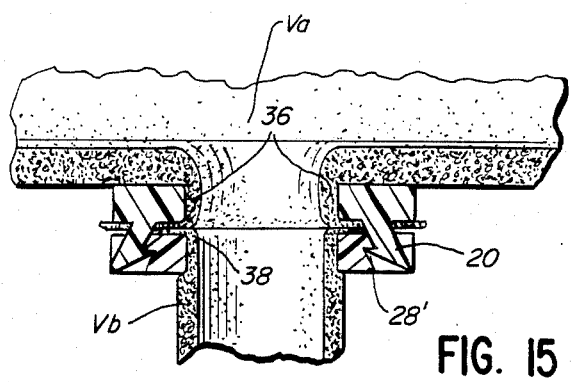
FIG. 15 is a sectional view of the same section in FIG. 14 and illustrating the interlocking of couplers in the completed end-to-side anastomosis of the main and the branch vessels.

Referring again to FIG. 1, the coupler 10 includes four cavities 26 extending through faces 16 and 18. The cavities 26 interrupt the peripheral surface 14. Within each cavity 26, an integral canted projection extends from the bottom of the cavity 26 radially outward to form a wedge 28 which matingly conforms to the shoulder 25 in the hooks 20 projecting from a second coupler 10'. As best illustrated in FIGS. 7 and 15, the wedge 28' of a second coupler 10' interlocks with the hook 20 projecting from the first coupler 10 when the anastomosis is completed.

Figure 3:
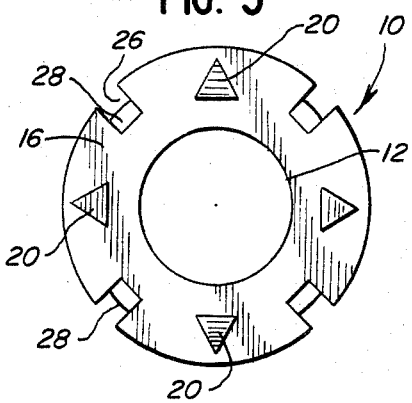
FIG. 3 is an end view of the device of FIG. 2 and illustrating the front face from which the hook members project, and further illustrating alternating receptor cavities selectively spaced along peripheral surface of the coupler.
Figure 4:
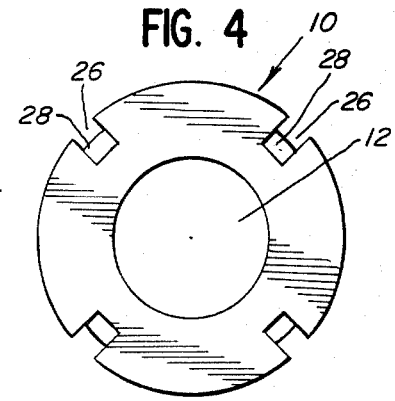
FIG. 4 is an end view of the rear face of the device and illustrating the cavities shown in FIG. 3 passing through the rear face as well as the front face of the coupler.

FIG. 3 illustrates an end view of the front face 16 on which hooks 20 and wedges 28 are arranged in alternating positions along a generally circular pattern. The hooks 20 are spaced so that a pair of hooks are positioned in opposing positions on a diameter of face 16 in order to provide mechanical balance in fixing the vessel tissue on the hooks 20. Similarly, the wedges 28 which interlock with the hooks 20' from the second coupler 10' are positioned in diametral opposition. As illustrated in FIG. 4, only the cavities 26 and wedges 28 are visible in an end view of the rear face 18.

Figure 5:
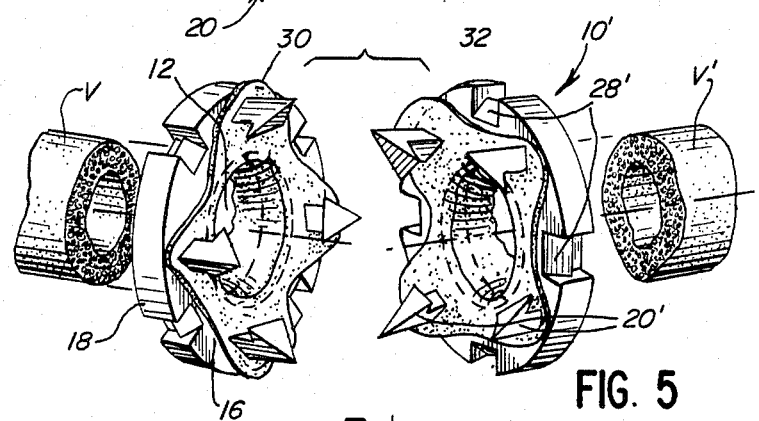
FIG. 5 is a perspective view illustrating the eversion and penetration by the hook members of the two ends of tubular vessels to be joined in an end-to-end anastomosis employing two of the couplers of FIG. 1.
Figure 6:
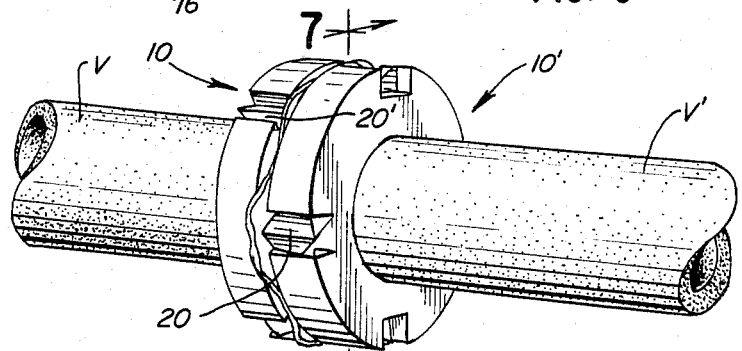
FIG. 6 is a perspective view of the completed anastomosis of FIG. 5 and illustrating the two coupler devices interlocked to join the everted vessel ends.
Figure 7:
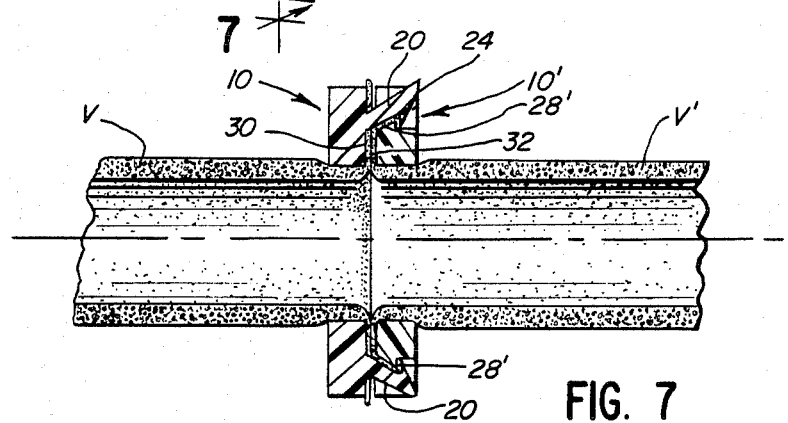
FIG. 7 is a sectional view taken along the line 7—7 of FIG. 6 and in a direction indicated generally.

FIGS. 5, 6 and 7 will be referred to in the description of the anastomosis procedure employing coupler devices 10 and 10' to join two ends of a severed tubular vessel, such as bile ducts, vas deferens, fallopian tubes, as well as blood vessels and ureters.

Referring to FIG. 5, one end 30 of a severed vessel V is passed through the bore 12 from the rear face 18 and then, through the front face 16. The emergent end 30 is then folded or everted backwardly and across the front face 16, and the resulting everted end is fixed upon the coupler device 10 by forcing the end back until it is penetrated by each sharpened tang or barb of each head 24. The interior surface of the vessel is thus exposed upon the front surface 16 of the device 10. This procedure is repeated with the end 32 of the vessel V' to fix the eversion thereof upon a second coupler 10'. The interior surfaces of the everted vessels V and V' are then engaged in direct, clamped contract by interlocking couplers 10 and 10' so that the hook members of coupler 10 are locked or retained on the wedges 28' of coupler 10', as illustrated in FIG. 6. In the interlocking operation, the approaching hook 20 is resiliently displaced by the initial sliding engagement with the wedge 28' until the head 24 clears the wedge 28'. Thereafter, shoulder 25 snaps behind the wedge 28' so that the shoulder 25 is retained in engagement with the wedge 28' to prevent retraction of the hook 22. This maintains interlocking of the couplers 10 and 10' as illustrated in FIG. 7. The everted intima of the ends 30 and 32 are thus clamped together between the interlocked coupler 10 and 10' and the resulting patency produces healing of the reunited vessels V and V' without any suturing trauma to the tissues. Since the coupler 10 and 10' are left in place after closing their composition will be of an inert material, such as stainless steel or a non-toxic material, which is absorbable by the body.

Figure 8:
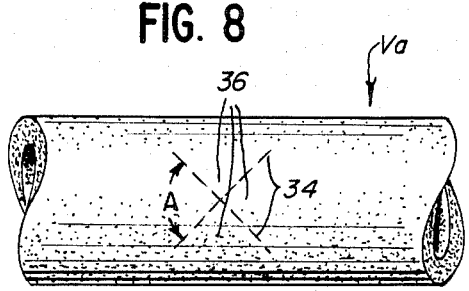
FIG. 8 is a plan view of the sidewall of a main vessel and illustrating incisions made through the sidewall in preparation for an end-to-side anastomosis employing the device of FIG. 1.
Figure 9:
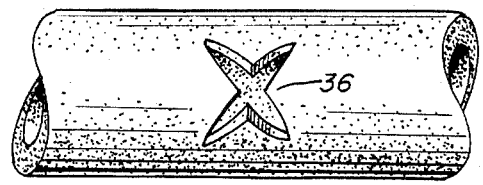
FIG. 9 is a plan view of the vessel of FIG. 8 and illustrating the partial, outward folding of the sidewall from the incisions to form flaps therein.
Figure 10:
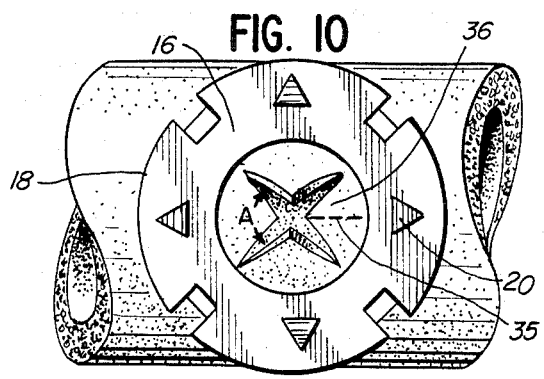
FIG. 10 is an enlarged plan view of the vessel in FIG. 9 and illustrating placement of a coupler on the vessel so that the flaps are generally circumscribed by a bore of the coupling device.
Figure 11:
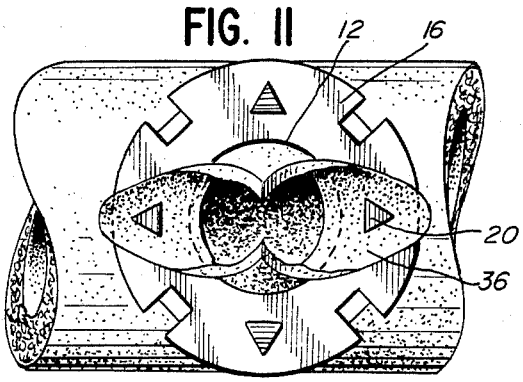
FIG. 11 is a plan view similar to FIG. 10 and illustrating outward eversion of the flaps through the bore and the penetration of two of the flaps by respective hook members.
Figure 12:
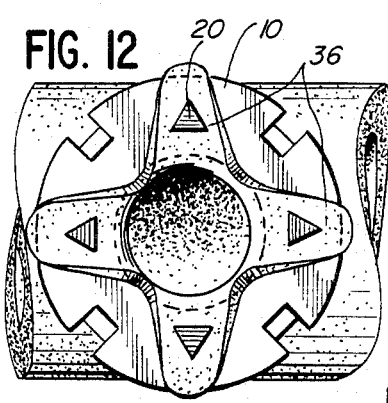
FIG. 12 is a plan view of the vessel in FIG. 11 and illustrating the fully everted flaps exposing the intima of the flap tissue fixed upon the coupler.

The couplers 10 and 10' can also be employed in "end-to-side" anastomosis to couple the end of a tubular vessel to the side of another vessel as described with reference to FIGS. 8 and 15. Referring to 8, the sidewall of a main vessel $V_a$, is cut through in a cruciform pattern of cuts 34 producing four, foldable flps 36 in the sidewall tissue of a vessel $V_a$, as illustrated in FIG. 7. A coupler 10 is then placed so that the rear face 18 engages the vessel $V_a$ with the alignment of the bore 12 generally circumscribing the flaps 36, as illustrated in FIG. 10. The coupler 10 is placed so that each hook 20 is generally aligned along a line 35 which bisects the angle A between cuts 34 in order to permit generally central penetration of the flap 36 by the respective hook 20 for even and secure fixation of the flaps on the coupler 10. Thereafter, each of the four flaps 36 is everted outwardly through bore 12, as illustrated in FIG. 11. Each flap 36 is penetrated by a respective hook 20 to fix the flap on the front face 16. After each of the four everted flaps has been fixed, the front face 16 of the coupler 10 is substantially covered with flap tissue exposing the intima, as illustrated in FIG. 12.

Figure 13:
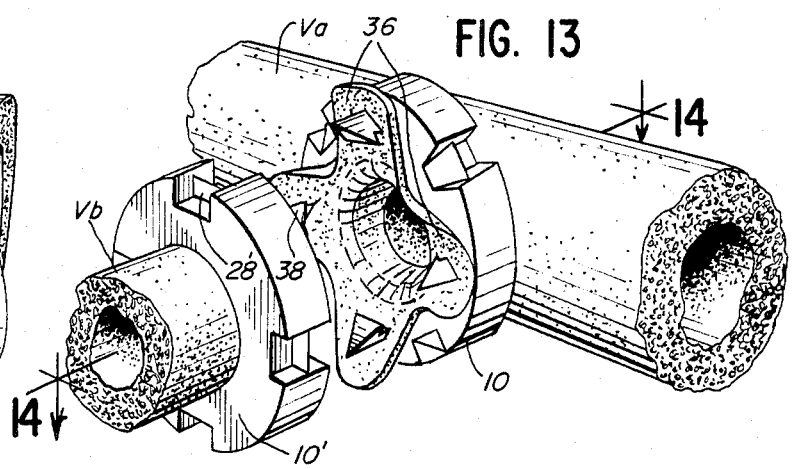
FIG. 13 is a perspective view illustrating the everted and fixed sidewall of the vessel of FIG. 12 and an everted and fixed end of a second or branch vessel upon a second coupler similar to FIG. 5.
Figure 14:
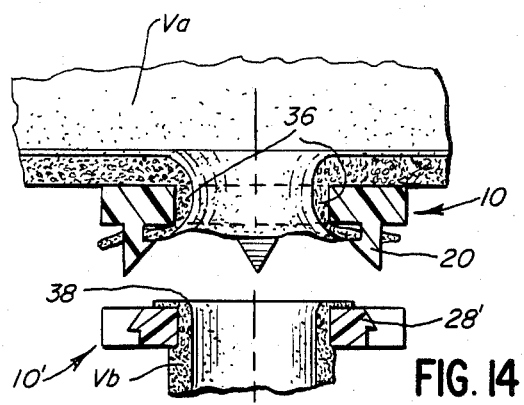
FIG. 14 is a sectional view taken along the line 14—14 of FIG. 13 and the direction indicated generally, and illustrating the alignment of the hook members penetrating the flaps of the main vessel and the wedge members of the coupler device fixed to the branch vessel.

Referring to FIG. 13, the end 38 of a second or branch vessel $V_b$ is everted and fixed on a second coupler 10' in the manner previously described with reference to FIG. 5, as illustrated in FIGS. 13 and 14. The couplers 10 and 10' can then be joined so that hooks 20 and 20' are interlocked with corresponding wedges 28' and 28. The intima of the flags 36 is thus clamped in engagement with the intima of the everted end 38 to complete anastomotic coupling of the end of branch vessel $V_b$ to the side of main vessel $V_a$. Again, suturing is eliminated.

It should be noted that the need for supplementary procedures to secure the coupling such as referenced in the prior art identified is avoided entirely. Furthermore, the surgeon's finger is not required to support or guide the joinder of the vessels. After eversion of the tissue flaps on the hook means, the cooperating coupling disc members need only be interlocked to complete the procedure. The integral interlocking hooks and receptors on each of the couplers are positioned equally spaced in alternating pattern so that the registration for coupling does not require cumbersome alignment.

It is believed that minor variations in dimension and configuration of cooperating parts can occur to the skilled artisan without departing from the thrust of the invention.

I claim:

1. A two piece anastomotic coupling device for either end-to-end or end-to-side anastomosis of tubular tissue vessels, comprising:
   a. a pair of disc-like coupling members, each having an outer radial face, a pair of oppositely disposed planar axial faces, and an axial bore through said axial faces communicating with said axial faces, and dimensioned to receive a vessel therein;
   b. a plurality of integral coupling projections extending from a first axial face of each said member, each of said projections comprising a shoulder and an anchoring means for everted purchase thereon of a vessel passing through said bore;
   c. receptor means for each coupling projection located on the other said member, said receptor means comprising a plurality of recesses in the outer radial face and the adjacent portion of at least said first axial face of said member, said recesses projecting radially inwardly from said outer radial face, the number of said recesses being at least equal to the number of coupling projections on the other said member, each said recess carrying a shoulder on at least one surface thereof which shoulder is dimensioned to receive the shoulder of said projection in coupling relationship;
   whereby placement of said members in an aligned first axial face-to-first axial face relationship results in coupling of each said projection with a receptor means, and maintains the everted vessel parts in contact between said first axial faces.

2. A coupling device as described in claim 1 in which each of said projections has a hook-like formation including a tapered end for engaging such tissue and a shoulder for matingly engaging a shoulder of the receptor means for interlocking therewith.

3. A coupling device according to claim 2, wherein coupling of each said projection with a receptor means takes place by means of resilient outward deformation of said projection when the shoulder of said projection engages the shoulder of the receptor means, followed by engagement of the shoulder of said projection behind the shoulder of said receptor means.

4. The devices as claimed in claim 1, wherein said plurality of projections and receptor means are arranged in alternating positions along a generally circular pattern on said first axial face of each said member.

5. The devices as claimed in claim 4 wherein said projections and receptor means are equally spaced in said pattern.

6. A method for end-to-side anastomotic coupling of the open end of a tubular tissue vessel to an opening in the side of another tubular tissue vessel comprising the steps of:
   A. incising the sidewall of a first vessel between remote ends thereof to produce an opening in the sidewall providing a plurality of flaps thereat;
   B. placing a first coupling device having an axial bore therethrough over said flaps;
   C. passing the end of each flap through said axial bore to protrude outwardly thereof;
   D. everting the flap ends to expose the interior surface of the vessel flaps and anchoring said everted flaps upon said coupling devices;
   E. passing the open end of another vessel through an axial bore formed in a second like coupling device;
   F. everting the open end of said second vessel and anchoring the everted end upon said second coupling device; and
   G. joining said first and second coupling devices to maintain the everted flaps of said first vessel engaged with the everted end of said second vessel in order to produce permanent intraluminal anastomosis thereof.

7. The method as claimed in claim 6 wherein said joining comprises interlocking integral coupling members formed on said respective coupling devices.

* * * * *